United States Patent
Perez-Pacheco et al.

(10) Patent No.: US 11,744,950 B2
(45) Date of Patent: Sep. 5, 2023

(54) CONTROLLED DISPENSE SYRINGE

(71) Applicant: AMGEN INC., Thousand Oaks, CA (US)

(72) Inventors: Joel Perez-Pacheco, Camarillo, CA (US); Lawrence Scott Ring, Laguna Beach, CA (US)

(73) Assignee: AMGEN INC., Thousand Oaks, CA (US)

( * ) Notice: Subject to any disclaimer, the term of this patent is extended or adjusted under 35 U.S.C. 154(b) by 282 days.

(21) Appl. No.: 16/969,691

(22) PCT Filed: Feb. 12, 2019

(86) PCT No.: PCT/US2019/017607
§ 371 (c)(1),
(2) Date: Aug. 13, 2020

(87) PCT Pub. No.: WO2019/173026
PCT Pub. Date: Sep. 12, 2019

(65) Prior Publication Data
US 2021/0001052 A1    Jan. 7, 2021

Related U.S. Application Data

(60) Provisional application No. 62/639,754, filed on Mar. 7, 2018.

(51) Int. Cl.
*A61M 5/315* (2006.01)
*A61M 5/31* (2006.01)

(52) U.S. Cl.
CPC ...... *A61M 5/31501* (2013.01); *A61M 5/3129* (2013.01)

(58) Field of Classification Search
CPC .......... A61M 5/31501; A61M 5/31505; A61M 2005/31506; A61M 2005/31508;
(Continued)

(56) References Cited

U.S. PATENT DOCUMENTS

| | | | |
|---|---|---|---|
| 3,563,240 A | | 2/1971 | Silver |
| 5,385,558 A | * | 1/1995 | Cottone, Sr. ...... A61M 5/31591 604/225 |

(Continued)

FOREIGN PATENT DOCUMENTS

| | | |
|---|---|---|
| EP | 0022987 A1 | 1/1981 |
| GB | 1007328 A | 10/1965 |
| GB | 1534229 A | 11/1978 |

OTHER PUBLICATIONS

International Search Report and Written Opinion for International Application No. PCT/US2019/017607, dated Apr. 16, 2019.

*Primary Examiner* — Amber R Stiles
*Assistant Examiner* — Leah J Swanson
(74) *Attorney, Agent, or Firm* — MARSHALL, GERSTEIN & BORUN LLP

(57) ABSTRACT

A syringe is described with a plunger assembly that is adapted to have a dispensing stroke sized to dispense a fluid therapeutic product from the syringe without dispensing any air or headspace. The syringe includes a plunger rod having a stop feature that stops a dispensing stroke of the plunger rod at a distance corresponding to a level of air or headspace within the syringe avoiding additional air dispensing steps from a healthcare provider.

20 Claims, 3 Drawing Sheets

(58) Field of Classification Search
CPC .......... A61M 2005/3151; A61M 5/002; A61M 2209/06; A61M 5/36; A61M 5/31591; A61M 5/3129; A61M 5/3134; A61M 5/3135; A61M 2005/3123; A61M 2005/3132; A61M 2005/31516; A61M 2005/31523

See application file for complete search history.

(56) References Cited

U.S. PATENT DOCUMENTS

| | | | |
|---|---|---|---|
| 7,789,862 B2 * | 9/2010 | Thorne, Jr. | A61M 5/284 604/231 |
| 9,101,719 B2 * | 8/2015 | Vernizeau | A61M 5/002 |
| 2005/0215957 A1 | 9/2005 | Hynes | |
| 2012/0245530 A1 * | 9/2012 | Oden | A61M 5/31535 604/189 |
| 2016/0175537 A1 | 6/2016 | Thorne, Jr. et al. | |
| 2018/0250474 A1 * | 9/2018 | Wei | A61M 5/3137 |

* cited by examiner

CONTROLLED DISPENSE SYRINGE

CROSS-REFERENCE TO RELATED APPLICATION

Priority is claimed to U.S. Provisional Patent Application No. 62/639,754, filed Mar. 7, 2018, the entire contents of which are incorporated herein by reference.

FIELD OF THE DISCLOSURE

The present disclosure generally relates to syringes and, more particularly, to prefilled syringes.

BACKGROUND

For some drug dispensing devices, a healthcare provider is required to transfer a therapeutic product from a prefilled syringe to a cartridge or device reservoir that is configured for the drug dispensing device. Typically, a prefilled syringe is filled with a predetermined amount of the therapeutic product along with a predetermined amount of air. To transfer the therapeutic product to the cartridge or device reservoir, a healthcare provider can orient the prefilled syringe so that the air is adjacent to the needle and depress a plunger of the prefilled syringe to dispense the air. This air dispensing operation may inadvertently dispense some of the therapeutic product, which can waste an expensive product and may cause the amount of therapeutic product in the prefilled syringe to fall below a prescribed amount for the patient. On the other hand, if the air is not fully dispensed from the prefilled syringe, some air may be transferred to the cartridge or device reservoir. Air within a fluid flow path of the drug dispensing device can negatively impact the operation of the device, such as by causing uncontrolled forward or backward flow due to barometric pressure changes.

SUMMARY

In accordance with a first exemplary aspect, a syringe is disclosed that includes a barrel that has an interior, a dispensing opening at a distal end, and an open proximal end having an end surface. A stopper is disposed within the interior of the barrel. The syringe further includes a plunger rod that has a first end operably coupled to the stopper and a second end that extends through the open proximal end of the barrel. The plunger rod is configured to be engaged by a user to drive the stopper through the barrel to thereby dispense contents within the barrel through the dispensing opening during a dispensing operation. The plunger rod further includes an outwardly projecting stop that is adjacent the second end. The barrel is configured to contain a fluid therapeutic product. Headspace between the dispensing opening and the stopper and the stop of the plunger rod is configured to engage the end surface of the open proximal end of the barrel to stop movement of the plunger rod during the dispensing operation so that the headspace is left within the barrel.

In accordance with a second exemplary aspect, a syringe is disclosed that includes a barrel that has an interior, a dispensing opening at a distal end, and an open proximal end having an end surface. A stopper is disposed within the interior of the barrel. The syringe further includes a plunger rod that has a first end operably coupled to the stopper and a second end that extends through the open proximal end of the barrel. The plunger rod is configured to be engaged by a user to drive the stopper through the barrel to thereby dispense contents within the barrel through the dispensing opening during a dispensing operation. The plunger rod further includes an outwardly projecting stop that is adjacent the second end. In a first configuration with the stop of the plunger rod spaced from the end surface of the proximal end of the barrel a first distance, the barrel is configured to contain a fluid therapeutic product and headspace between the dispensing opening and the stopper. In a second configuration with the stop of the plunger rod abutting the end surface of the proximal end of the barrel and the stopper shifted the first distance within the interior of the barrel, the barrel contains the headspace.

In further accordance with the foregoing first and/or second aspects, a syringe may further include any one or more of the following preferred forms.

In accordance with one preferred form, the stop can have at least one radial dimension greater than a corresponding radius of an opening of the open proximal end of the barrel.

In accordance with one preferred form, the stop can include a portion having a diameter greater than a corresponding diameter of an opening of the open proximal end of the barrel such that the stop is configured to abut the end surface on opposing radial edge portions.

In accordance with one preferred form, the barrel can include a flange that extends around the open proximal end. The flange is configured to be gripped by a user during the dispensing operation and provide the end surface for engagement with the stop of the plunger rod.

In accordance with one preferred form, the syringe can further include a needle that is fluidly coupled to the interior of the barrel at the dispensing opening.

In accordance with one preferred form, the plunger rod can further include a thumb rest portion at the second end. In accordance with a further preferred form, the thumb rest portion can be spaced from the stop.

In accordance with one preferred form, the syringe can further include the fluid therapeutic product disposed within the barrel.

In accordance with one preferred form, the syringe the stop and plunger rod can be separate components and the syringe can further include a securing mechanism that is configured to couple the stop and the plunger rod together. In accordance with a further preferred form, the syringe can be provided in combination with a storage container, where the storage container is configured to engage the securing mechanism so that the stop and plunger rod are in an uncoupled configuration when the syringe is disposed within the storage container.

In accordance with a third exemplary aspect, a method of filling a syringe with a fluid therapeutic product is disclosed that includes filling a barrel of the syringe with a dose of fluid therapeutic product, disposing a stopper within the barrel to contain the dose within the syringe along with a headspace, and providing a plunger rod having an outward projecting stop and a length. The plunger being configured so that, with the plunger rod coupled to the stopper, the stop is spaced from an end of the barrel a distance corresponding to depth of the headspace in the barrel.

In accordance with a fourth exemplary aspect, a method of dispensing a predetermined amount of fluid therapeutic product from a syringe is disclosed that includes engaging a thumb rest of a plunger rod of the syringe, where the plunger rod extends into a barrel of the syringe to couple to a stopper disposed within the barrel. The method further includes pushing the thumb rest of the plunger rod toward the barrel of the syringe to thereby drive the stopper through the barrel which dispenses the fluid therapeutic product through a needle of the syringe fluidly coupled to the barrel and abutting a stop of the plunger rod with an end surface of the barrel, thereby stopping movement of the stopper and preventing any headspace within the barrel from being expelled.

In accordance with one preferred form, the method can further include agitating the barrel with the barrel in a generally vertical orientation to with the thumb rest above the barrel to ensure that all of the headspace is above the fluid therapeutic product prior to pushing the thumb rest of the plunger rod toward the barrel.

In accordance with one preferred form, engaging the thumb rest can include engaging an end portion of the plunger rod spaced from the stop.

In accordance with one preferred form, the method can further include removing the syringe from a storage container to cause a securing mechanism to couple the plunger rod and stop together.

BRIEF DESCRIPTION OF THE DRAWINGS

The above needs are at least partially met through provision of the embodiments described in the following detailed description, particularly when studied in conjunction with the drawings, wherein.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

A syringe is provided with a plunger assembly that is adapted to have a dispensing stroke sized to dispense a fluid therapeutic product from the syringe without dispensing any air or headspace. More specifically, the syringe includes a plunger rod having a stop feature that stops a dispensing stroke of the plunger rod at a distance corresponding to a level of air or headspace within the syringe.

Figure 1:
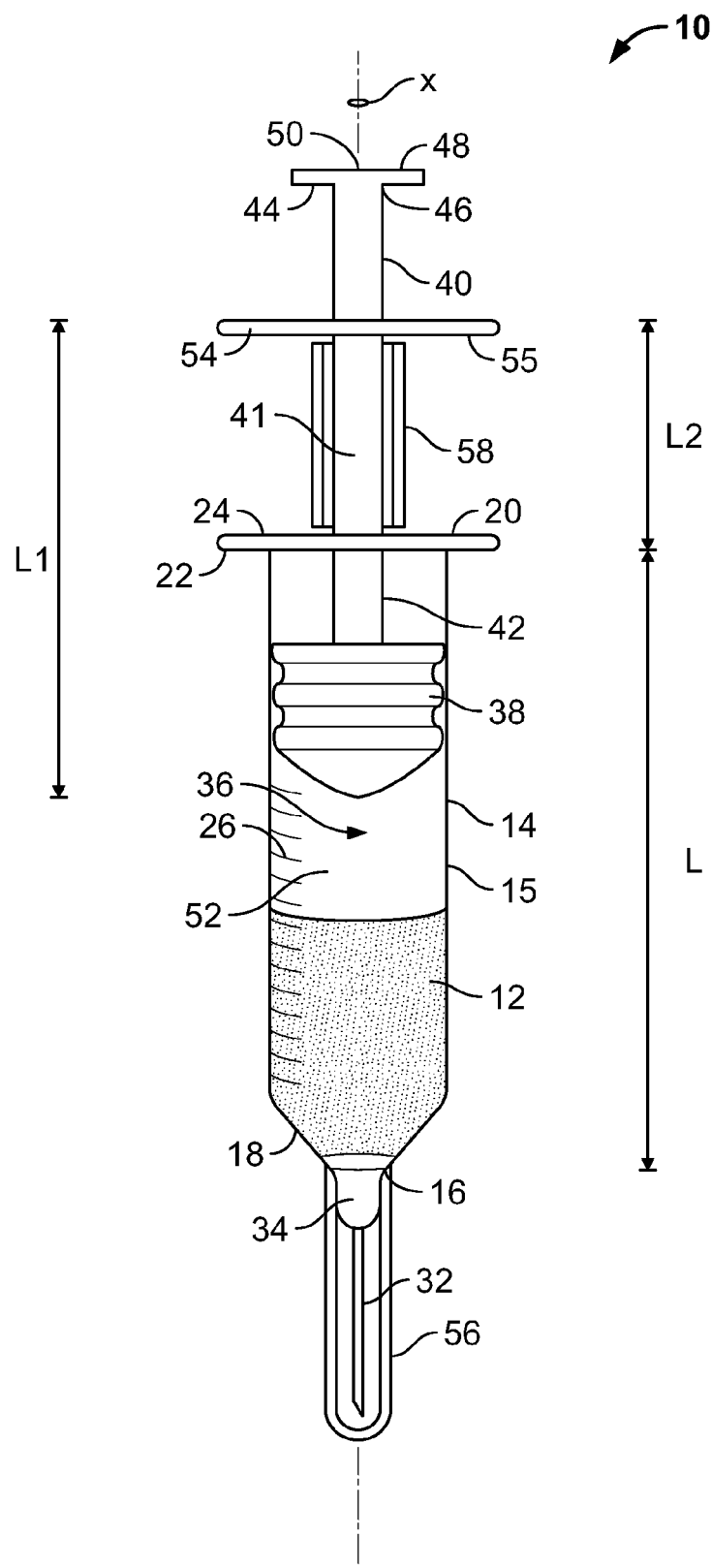
FIG. 1 illustrates a syringe in a full configuration showing a fluid therapeutic product and headspace within a barrel in accordance with various embodiments of the present disclosure.

Referring now to the drawings, FIG. 1 shows a syringe 10 extending along a longitudinal axis X. The syringe 10 is illustrated in a pre-filled state having a dose or other predetermined amount of a fluid therapeutic product 12 contained within a barrel or reservoir 14. The barrel 14 has tubular configuration oriented along the longitudinal axis X with an annular sidewall 15 extending between a dispensing opening 16 at a distal end 18 and an open proximal end 20. The proximal end 20 includes a radially projecting flange 22 that provides an upwardly facing end surface 24. If desired, the barrel 14 can include measurement markings 26 distributed along a length L thereof to provide a visual indication of the amount of product 12. The barrel 14 can be made of any suitable material, such as glass or a polymer.

At the distal end 18 of the barrel 14, the syringe 10 includes a needle 32 and a needle hub 34 coupled to the barrel 14, such that the needle 32 is fluidly coupled with an interior 36 of the barrel 14. The syringe 10 further includes a stopper (plunger-stopper) 38 and a plunger rod 40 engaging the stopper 38 and projecting outwardly through the open proximal end 20 of the barrel 14 along the longitudinal axis X. The plunger rod 40 includes an elongate body 41 that is coaxial with the barrel 14. The body 41 engages the stopper 38 at a distal end 42 and includes a thumb rest 44 at an opposite, proximal end 46. The plunger rod 40 can engage the stopper 38 by any suitable method, such as embedded therein, having mating components, abutting an end surface, and so forth. As shown, the thumb rest 44 can include a flange 48 that extends outwardly from the body 41 generally perpendicular to the longitudinal axis X providing a user with a flat or contoured upwardly facing engagement surface 50. So configured, a user can grip the flange 22 of the proximal end 20 of the barrel 14 with two fingers and the engagement surface 50 with a thumb to press down and drive the stopper 38 through the barrel 14 in a dispensing operation.

As shown, the barrel 14 also contains an air bubble or headspace 52 along with the product 12. Traditionally, a healthcare provider handles the syringe 10 so that the needle 32 is oriented upwardly and depresses the plunger rod 40 to drive the stopper 38 through the barrel 14 to dispense the air 52 through the needle 32 or eyes the level of product 12 during dispensing to avoid expelling air. The plunger rod 40 of the syringe 10 described herein avoids this operation by including a stop 54 that extends outwardly from the plunger rod body 41 generally perpendicular to the longitudinal axis X thereof. The stop 54 is sized to engage the end surface 24 of the barrel proximal end 20 during a dispensing operation. Specifically, the stop 54 has at least one radial dimension greater than a corresponding radius of the opening of the barrel proximal end 20. In one form, the stop 54 includes a portion having a diameter greater than a corresponding diameter of the opening of the barrel proximal end 20 such that the stop 54 abuts the end surface 24 on opposing radial edge portions 55. In some examples, the stop 54 can have an oval or track-shaped configuration where at least the larger diameter is greater than the corresponding diameter of the opening of the barrel proximal end 20. In another example, the stop 54 can have a circular configuration where the diameter is greater than the corresponding diameter of the opening of the barrel proximal end 20.

So configured, the stop 54 prevents further displacement of the plunger rod 40 and, thus, the stopper 38, through the barrel 14 so that the dispensing operation dispenses a predetermined volume. Although the plunger rod 40 of the illustrated form includes the stop 54 spaced from the thumb rest 44, it should be understood that a plunger rod can be configured so that the stop also provides the thumb rest.

Stated another way, by configuring the plunger rod 40 to have a predetermined length between the distal end 42 and the stop 54 that corresponds to a desired portion of the barrel 14, the syringe 10 can be preconfigured to dispense a specific volume of fluid. Advantageously, this can be utilized to avoid the problems associated with headspace within conventional pre-filled syringes by limiting a dispensing operation to a volume that prevents the air 52 from being expelled.

Figure 2:
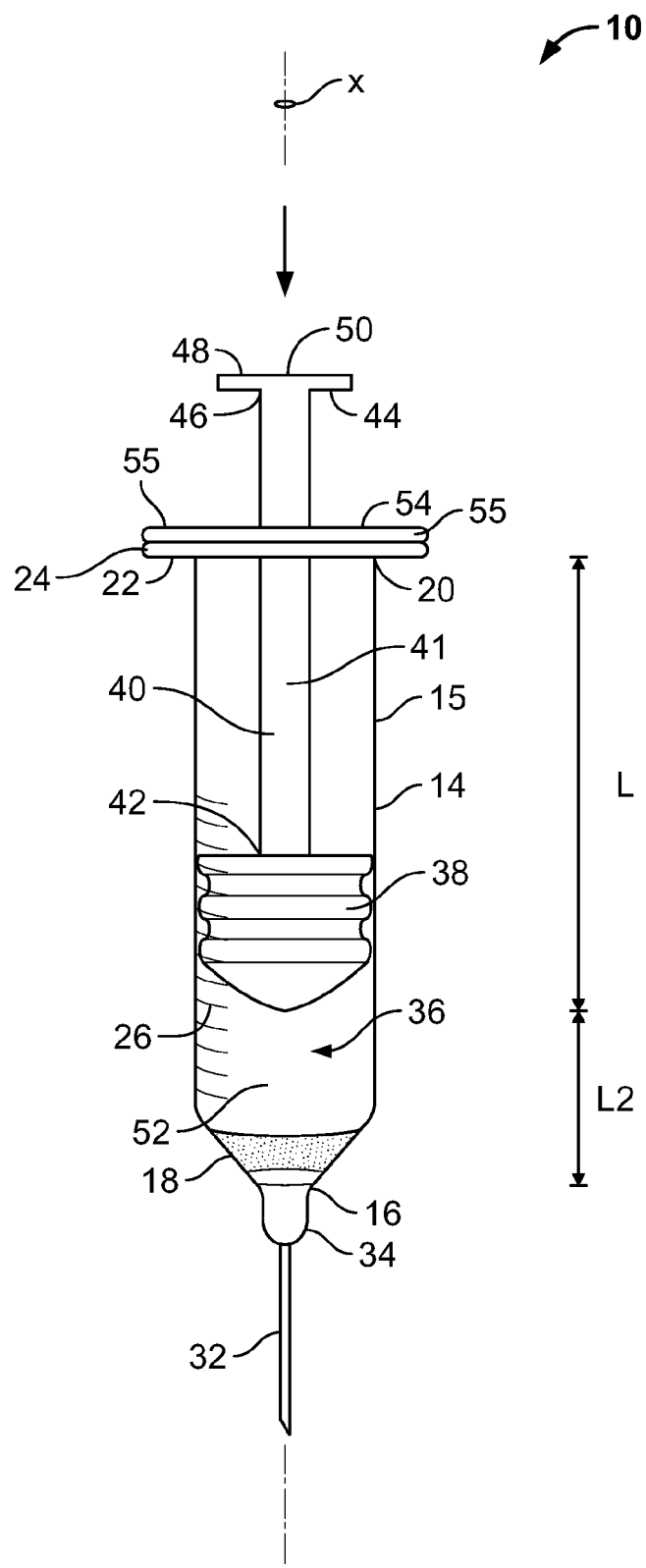
FIG. 2 illustrates a side elevation view of the syringe of FIG. 1 in a dispensed configuration in accordance with various embodiments of the present disclosure.

The predetermined length of the plunger rod 40 between the distal end 42 and the stop 54, combined with a length of the stopper 38, corresponds to a portion L1 of a length L of the barrel 14. This length L1 is shown in FIG. 2 with the plunger rod 40 fully inserted into the barrel 14 and the stop 54 abutting the end surface 24. Accordingly, during preparation of the syringe 10, the barrel 14 can be filled to a desired amount or dosage of the product 12 and the stopper 38 can be positioned within the barrel 14 so that the headspace 52 has a length, and corresponding volume, generally equal to a remaining portion L2 of the length L of the barrel 14.

Of course, as represented in the figures, the fluid of the product 12 may interact with the barrel 14 to have a meniscus rather than a flat top surface. In order to ensure that none of the air 52 is dispensed, the length L2 can have a value equal to or greater than a length of the therapeutic product 12 at its raised periphery adjacent to the barrel 14.

After the syringe 10 has been filled with the product 12, the syringe 10 can be packaged for transportation and storage. A storage configuration can include a removable needle guard or cap 56 and/or a removable collar 58 disposed between the barrel end surface 24 and the stop 54 to prevent undesired depression of the plunger rod 40.

When a user would like to dispense the product 12, the user can orient the syringe in a generally vertical orientation, e.g., within 45 degrees of vertical and preferably within 20 degrees of vertical, with the thumb rest 44 disposed above the barrel 13 and the needle 32 pointed downward. This orientation allows the product 12 to be positioned adjacent to the dispensing opening 16 with the headspace 52 positioned above the product 12. The user can then agitate the barrel 13, such as by tapping, or can pause a predetermine interval, such as about 10 seconds to about 1 minute, to ensure that all of the headspace 52 is above the product 12 before dispensing. Thereafter, the user can depress the plunger rod 40 to drive the stopper 38 through the barrel 14. Advantageously, as described above, the plunger rod 40 moves until the stop 54 abuts the end surface 24 of the barrel 14, stopping movement of the stopper 38 within the barrel 14. As shown in FIG. 2, the plunger rod 40 and barrel 14 are adapted so that this position of the plunger rod 14 and stopper 38 leaves the headspace 52 within the barrel 14 while dispensing the predetermined amount of the product 12.

Figure 3:
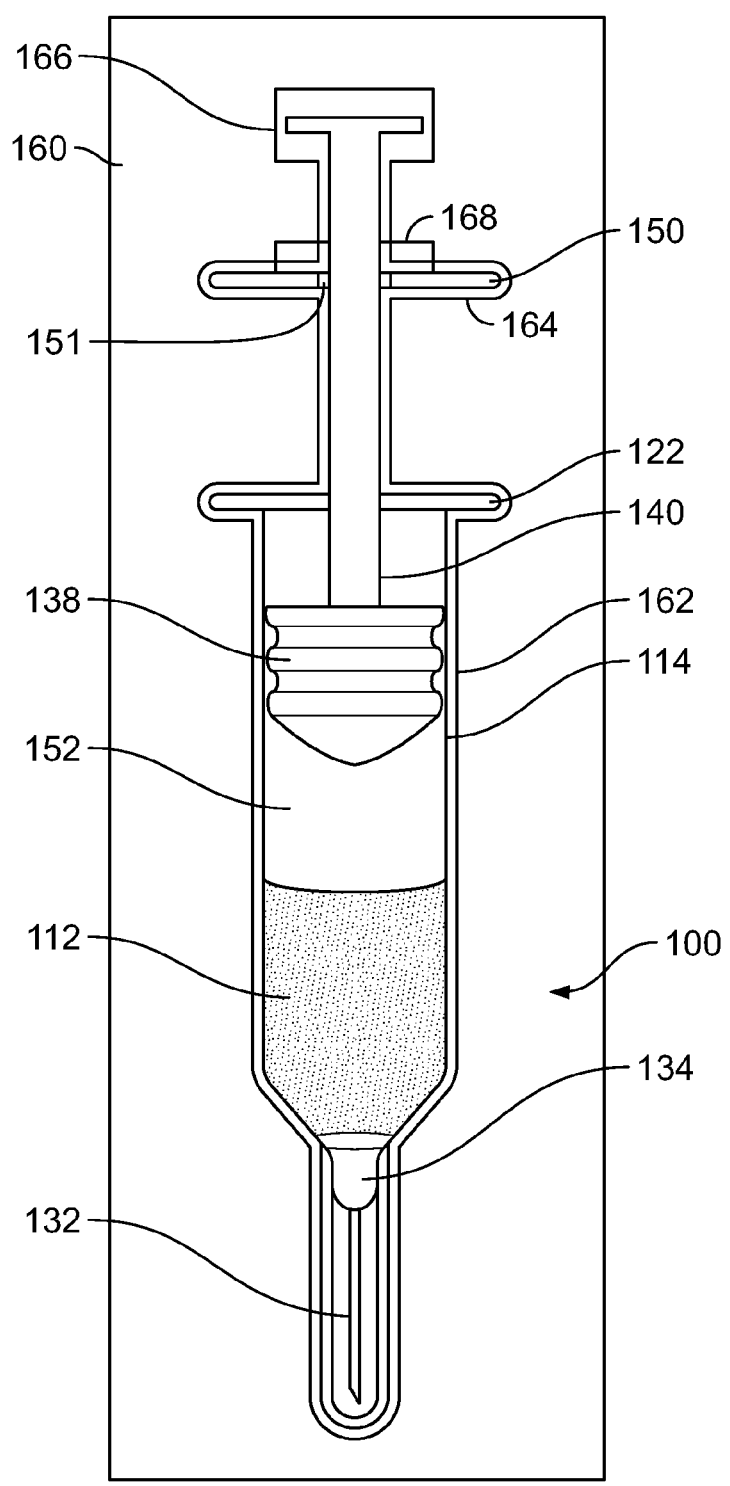
FIG. 3 illustrates a syringe in a full configuration stored in a tray in accordance with various embodiments of the present disclosure.

Another embodiment of a syringe 100 is shown in FIG. 3. This embodiment includes many features similar to the above embodiment shown in FIG. 1 and, thus, similar reference characters will be utilized for similar features. For example, the syringe 100 includes a barrel or reservoir 114 having a fluid therapeutic product 112 and headspace 152 therein, a needle 132, a needle hub 134, a stopper 138, a plunger rod 140, and so forth.

In this embodiment, the plunger rod 140 is coupled or otherwise secured to the stopper 138 and is separate from a plunger rod stop 150. Accordingly, absent a coupling, the plunger rod 140 can move freely with respect to the stop 150. For example, the stop 150 can include a central opening 151 extending therethrough that has a diameter or other dimension larger than the plunger rod 140.

As is understood, altitude changes can affect the headspace 152 in a prefilled syringe 100. For example, altitude changes can cause the stopper 138 to move and increase the volume of headspace 152. As a result, subsequent use of the delivery device can include injecting some air from the headspace into the patient subcutaneously. By providing a freely movable stop 150, the stop 150 can be positioned on the plunger rod 140 at a position corresponding to a length of the fluid therapeutic product 112 after any movement by the stopper 138 and plunger rod 140 during transport or storage.

By one approach, the syringe 100 can be stored in a tray or other storage container 160 having recesses 162, 164 that hold the barrel 114 and the stop 150, respectively, at static positions relative to one another. The recesses 162, 164 can be sized to frictionally engage the barrel 114 and stop 150 so that movement thereof is restricted. This ensures that the stop 150 is spaced from the barrel flange 122 a distance corresponding to the length of the product 112 regardless of any movement of the stopper 138 and plunger rod 140. The tray 160 can further include a recess 166 for the thumb rest 144 that provides clearance for any movement by the stopper 138 imparted on the plunger rod 140.

The syringe 100 can further include a securing mechanism 168 mounted on or incorporated into the plunger rod 140 and/or stop 150 that is engaged by the tray 160 when the syringe 100 is stored therein. The securing mechanism 168 includes a member or portion that is biased to engage the other of the plunger rod 140 or stop 150 to thereby hold the plunger rod 140 and stop 150 together so that the syringe 100 can dispense the product 112 as described with respect to the above embodiment. The securing mechanism 168 can include any desired biasing mechanism, such as a spring, pressurized gas, and so forth. The tray 160 engages the securing mechanism 168 so that the plunger rod 140 and stop 150 are held in an uncoupled state during storage, thereby allowing the plunger rod 140 to float and move in response to head space fluctuations that might occur as a result of altitude changes during transportation for example. When the syringe 100 is removed from the tray 160, however, the securing mechanism 168 automatically biases the member or portion to engage a corresponding member, portion, recess, etc. on the other of the plunger rod 140 or stop 150 so that the plunger rod 140 and stop 150 are secured together in a fixed relationship. Such a configuration can advantageously ensure that headspace fluctuations do not detrimentally effect the delivery of the drug.

In one example, the syringe 10, 100 described herein can provide a desired accuracy of fluid therapeutic product injection of +/−10 microliters. In a 1 mL syringe, the movement of the plunger can be controlled to +/−0.3 mm to achieve this desired accuracy.

The disclosure provided herein can be utilized with any desired dosage and syringe size, while ensuring a delivery amount for accurate dosages. This is particularly suitable for pre-filled syringes for patient self-injection. The components of the syringe 10, such as the barrel 14 and plunger rod 40, can be made of any suitable material, such as plastic or glass.

The above description describes various syringes, devices, assemblies, components, subsystems and methods for use related to drug delivery. The syringes, devices, assemblies, components, subsystems, methods or drug delivery devices can further comprise or be used with a therapeutic product (aka, a drug) including but not limited to those drugs identified below as well as their generic and biosimilar counterparts. The term therapeutic product or drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 146B7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); Vectibix® (panitumumab), Xgeva® (denosumab), Prolia® (denosumab), Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide®

(epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153, 507); Tysabri® (natalizumab, anti-α4integrin mAb); Valortim® (MDX-1303, anti-*B. anthracis* protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFR mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, or BPS 804 (Novartis) and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoVEXGALV/ CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BiTE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:
1. A syringe comprising:
 a barrel having an interior, a dispensing opening at a distal end, and an open proximal end having an end surface;
 a stopper disposed within the interior of the barrel;
 a plunger rod having a first end operably coupled to the stopper and a second end extending through the open proximal end of the barrel, the plunger rod configured to be engaged by a user to drive the stopper through the barrel to thereby dispense contents within the barrel through the dispensing opening during a dispensing operation; and
 an outwardly projecting stop coupled to the plunger rod adjacent the second end;
 wherein the barrel is configured to contain a fluid therapeutic product and a headspace between the dispensing opening and the stopper, and the stop is configured to engage the end surface of the open proximal end of the barrel to stop movement of the plunger rod during the dispensing operation so that the headspace is left within the barrel, a length of the headspace left within the barrel is substantially equal to a length of the plunger rod between the stop and the proximal end of the barrel before the dispensing operation.

2. The syringe of claim 1, wherein the stop has at least one radial dimension greater than a corresponding radius of an opening of the open proximal end of the barrel.

3. The syringe of claim 1, wherein the stop includes a portion having a diameter greater than a corresponding diameter of an opening of the open proximal end of the barrel such that the stop is configured to abut the end surface on opposing radial edge portions.

4. The syringe of claim 1, wherein the barrel includes a flange extending around the open proximal end, the flange configured to be gripped by a user during the dispensing operation and providing the end surface for engagement with the stop of the plunger rod.

5. The syringe of claim 1, further comprising a needle fluidly coupled to the interior of the barrel at the dispensing opening.

6. The syringe of claim 1, wherein the plunger rod further comprises a thumb rest portion at the second end spaced from the stop.

7. The syringe of claim 1, further comprising the fluid therapeutic product disposed within the barrel.

8. The syringe of claim 1, wherein the stop and plunger rod are separate components, and further comprising a securing mechanism configured to couple the stop and the plunger rod together.

9. The syringe of claim 8 in combination with a storage container, the storage container configured to engage the securing mechanism so that the stop and plunger rod are in an uncoupled configuration when the syringe is disposed within the storage container.

10. A syringe comprising:
a barrel having an interior, a dispensing opening at a distal end, and an open proximal end having an end surface;
a stopper disposed within the interior of the barrel;
a plunger rod having a first end operably coupled to the stopper and a second end extending through the open proximal end of the barrel, the plunger rod configured to be engaged by a user to drive the stopper through the barrel to thereby dispense contents within the barrel through the dispensing opening during a dispensing operation; and
an outwardly projecting stop coupled to the plunger rod adjacent the second end;
wherein, in a first configuration with the stop spaced from the end surface of the proximal end of the barrel a first distance, the barrel is configured to contain a fluid therapeutic product and a headspace between the dispensing opening and the stopper, and, in a second configuration with the stop abutting the end surface of the proximal end of the barrel and the stopper shifted the first distance within the interior of the barrel, the barrel contains the headspace, and a length of the headspace within the barrel in the second configuration is substantially equal to a length of the plunger rod between the stop and the proximal end of the barrel in the first configuration.

11. The syringe of claim 10, wherein the stop includes a portion having a diameter greater than a corresponding diameter of an opening of the open proximal end of the barrel such that the stop is configured to abut the end surface on opposing radial edge portions.

12. The syringe of claim 10, wherein the barrel includes a flange extending around the open proximal end, the flange configured to be gripped by a user during the dispensing operation and providing the end surface for engagement with the stop of the plunger rod.

13. The syringe of claim 10, further comprising a needle fluidly coupled to the interior of the barrel at the dispensing opening.

14. The syringe of claim 10, wherein the plunger rod further comprises a thumb rest portion at the second end spaced from the stop.

15. The syringe of claim 10, further comprising the fluid therapeutic product disposed within the barrel.

16. The syringe of claim 10, wherein the stop and plunger rod are separate components, and further comprising a securing mechanism configured to couple the stop and the plunger rod together.

17. A method of filling a syringe with a fluid therapeutic product, the method comprising:
filling a barrel of the syringe with a dose of fluid therapeutic product;
disposing a stopper within the barrel to contain the dose within the syringe along with a headspace;
providing a plunger rod coupled to the stopper; and
coupling an outwardly projecting stop to the plunger rod at a length configured so that the stop is spaced from an end of the barrel a distance corresponding to depth of the fluid therapeutic product in the barrel such that a length of the headspace left within the barrel during a dispensing operation is substantially equal to the length of the plunger rod between the stop and the proximal end of the barrel before the dispensing operation.

18. A method of dispensing a predetermined amount of fluid therapeutic product from a syringe, the method comprising:
engaging a thumb rest of a plunger rod of the syringe, the plunger rod extending into a barrel of the syringe to couple to a stopper disposed within the barrel;
pushing the thumb rest of the plunger rod toward the barrel of the syringe to thereby drive the stopper through the barrel which dispenses the fluid therapeutic product through a needle of the syringe fluidly coupled to the barrel;
abutting a stop coupled to the plunger rod with an end surface of the barrel, thereby stopping movement of the stopper, stopping a dispensing stroke of the plunger rod at a distance corresponding to a level of headspace within the barrel, and preventing any headspace within the barrel from being expelled, and wherein a length of the headspace left within the barrel after dispensing is substantially equal to a length of the plunger rod between the stop and the proximal end of the barrel before abutting the stop with the end surface of the barrel.

19. The method of claim 18, further comprising agitating the barrel with the barrel in a generally vertical orientation with the thumb rest above the barrel to ensure that all of the headspace is above the fluid therapeutic product prior to pushing the thumb rest of the plunger rod toward the barrel.

20. The method of claim 18, further comprising removing the syringe from a storage container to cause a securing mechanism to couple the plunger rod and stop together.

* * * * *

UNITED STATES PATENT AND TRADEMARK OFFICE
CERTIFICATE OF CORRECTION

PATENT NO. : 11,744,950 B2
APPLICATION NO. : 16/969691
DATED : September 5, 2023
INVENTOR(S) : Joel Perez-Pacheco et al.

Page 1 of 1

It is certified that error appears in the above-identified patent and that said Letters Patent is hereby corrected as shown below:

In the Claims

At Column 12, Line 30, "barrel" should be -- barrel, --.

Signed and Sealed this
First Day of October, 2024

Katherine Kelly Vidal
*Director of the United States Patent and Trademark Office*